United States Patent [19]

Oka

[11] Patent Number: 4,588,617
[45] Date of Patent: May 13, 1986

[54] PROCESS FOR PRODUCING CURED EPOXY RESIN SPHERICAL PARTICLES

[75] Inventor: Koichiro Oka, Ibaraki, Japan

[73] Assignee: Toray Industries, Inc., Tokyo, Japan

[21] Appl. No.: 651,362

[22] Filed: Sep. 17, 1984

[51] Int. Cl.$^4$ .................. B05D 1/18; C08L 63/00; D06P 5/00

[52] U.S. Cl. .................. 427/443.1; 523/414; 523/420; 528/88; 528/93; 528/111; 528/118; 528/123; 528/124; 8/506

[58] Field of Search .................. 523/414, 420; 528/121, 528/118, 111, 123, 124, 88, 93; 427/222, 443.1, 304, 306; 428/403; 8/506; 525/523

[56] References Cited

U.S. PATENT DOCUMENTS 4,446,257  5/1984  Kooijmans et al. .................. 523/420

*Primary Examiner*—Lewis T. Jacobs

*Attorney, Agent, or Firm*—Armstrong, Nikaido, Marmelstein & Kubovcik

[57] ABSTRACT

Spherical particles of cured epoxy resin having an average size not larger than 50 $\mu$m can be produced by adding a water-soluble amine curing agent to an emulsion of uncured epoxy resin.

It is possible to prepare spherical particles incorporating a UV absorber or inorganic particles, to dye these particles with an acid dye, and to subject them to electroless plating.

In addition, after-treatment of the cured particles enhances their heat resistance and destroys the epoxide groups left unreacted inside each particle.

These particles may be used as an ingredient of cosmetic and coating compositions, as a toner of electrostatic copiers, and for other applications.

15 Claims, No Drawings

PROCESS FOR PRODUCING CURED EPOXY RESIN SPHERICAL PARTICLES

BACKGROUND

(1) Field of the Invention

This invention relates to a process for producing cured epoxy resin spherical particles. More particularly, it relates to a process for producing spherical particles of cured epoxy resin having an average particle size not larger than 50 μm, which comprises adding an amine curing agent to a previously prepared emulsion of an uncured epoxy compound.

(2) Description of the Prior Art

Japanese Patent Publication No. 42360 (1978) teaches a method of producing fine particles of epoxy resin, in which a mixture of an epoxy compound having at least two epoxide groups in the molecule and a curing agent for epoxy resin is treated, in the presence or absence of a solvent or diluent for epoxy resin, in a dispersion medium in which said epoxy compound is insoluble or sparingly soluble, such as water and n-hexane, to form spherical particles of cured product. More precisely, a compound having at least two epoxide groups in the molecule is precured by the action of a curing agent in the presence or absence of a solvent or diluent for epoxy resin, and the precured product thus obtained is dispersed with stirring in water or n-hexane containing a surface-active agent or a water-soluble polymer that serves as a protective colloid, followed by heating of the resulting dispersion to ensure complete cure. However, the size of particles obtained by this technique is generally large, and it is difficult to achieve a particle size less than 50 μm.

SUMMARY

A primary object of this invention is to offer a process for producing spherical particles of cured epoxy resin having a particle size not larger than 50 μm. A second object of this invention is to offer a process for producing spherical particles of cured epoxy resin, which comprises adding a water-soluble amine to a previously prepared aqueous emulsion of an uncured epoxy compound. A third object of this invention is to offer a process for producing fine particles of epoxy resin in which an ultraviolet absorber or other compound bearing a functional group capable of reacting with epoxide group is chemically combined. A fourth object of this invention is to offer a process for producing fine particles of epoxy resin with an ultraviolet absorber, or inorganic or organic particles, mixed therein. A fifth object of this invention is to provide a process for producing fine particles of epoxy resin colored with a dye or subjected to electroless plating. A sixth object of this invention is to provide a process for producing fine particles of epoxy resin that can be used as an ingredient for cosmetic products, surface coatings and plastics, as a toner for electrostatic copiers, or for other purposes.

These objects can be achieved by emulsifying an uncured epoxy compound in water in the presence of a surface-active agent, followed by addition of a water-soluble amine to the resulting emulsion, thereby forming cured epoxy resin spherical particles having an average particle size not larger than 50 μm.

DETAILED DESCRIPTION OF THE INVENTION

The uncured epoxy compound used for the process of this invention should preferably be the one composed mainly of a compound having at least two epoxide groups in the molecule. Uncured epoxy compounds commonly used as adhesives satisfy this requirement. Typical examples include the following.

As compounds having two epoxide groups in the molecule may be mentioned, among others, bisphenol-A type diglycidyl ether, polyethylene glycol diglycidyl ethers, polypropylene glycol diglycidyl ethers, neopentyl glycol diglycidyl ether, 1,6-hexanediol diglycidyl ether, bisphenol-H type diglycidyl ether, and diglycidyl ethers of bisphenol alkylene-oxide adducts.

As compounds having three or more epoxide groups in the molecule may be mentioned, among others, glycerol triglycidyl ether, trimethylolpropane triglycidyl ether, polyglycidyl ethers of phenol-novolak type compounds, trisepoxypropyl isocyanurate, N,N,N',N'-tetraglycidyl-m-xylylenediamine, and 1,3-bis(N,N-diglycidylaminomethyl)cyclohexane.

Of these, bisphenol-A type glycidyl ether, bisphenol-H type glycidyl ether and polyglycidyl ethers or phenol-novolak type compounds are likely to give spherical particles and are therefore more advantageous for the purpose of this invention.

The uncured epoxy compound used in this invention should preferably be the one which contains compound having at least two epoxide groups in the molecule as described above in an amount of 50 to 100% by weight, alone or in combination.

The uncured epoxide compound of this invention may contain a compound having one epoxide group in the molecule in an amount not larger than 50% by weight. As examples of such compounds may be mentioned, among others, monoglycidyl ethers of aliphatic alcohols, such as 2-ethylhexyl glycidyl ether and 2-methyloctyl glycidyl ether, and monoglycidyl ethers of phenols, such as phenyl glycidyl ether. The compounds having one epoxide group in the molecule may also contain an ethylenic double bond. If the amount of the compound having one epoxide group in the molecule exceeds 50% by weight, sufficient polymerization or cross-linking may not be achieved in the curing step, resulting in the formation of particles with low mechanical strength or of tacky particles.

The compound having at least two epoxide groups used in this invention may also be a chemically modified product thereof, in which another compound having a functional group capable of reacting with the epoxide group has been chemically combined.

Such compounds that can chemically modify epoxy compounds include those containing alcoholic hydroxyl, mercapto, phenolic hydroxyl, carboxyl, and primary or secondary amino groups, sodium bisulfite, hydrogen halides, nitric acid and water, which may be properly selected depending on the intended purpose of modification (imparting the final particles with ultraviolet absorptive power, etc.). Reaction with the epoxide group can be effected under conditions commonly employed. When an alcoholic hydroxyl, phenolic hydroxyl, carboxyl or amino group is used for modification, the reaction is carried out preferably at 100° C. or higher temperatures. Addition of a catalyst, such as a tertiary amine, is favorable in some cases, for example, in the reaction of alcoholic hydroxyl group. Presence of sulfuric acid or other suitable capalyst is preferable when water is used for modification.

Typical examples of the compounds that can be used for modification of the epoxy compounds used for the process of this invention include dyes containing phenolic hydroxyl or amino group for the preparation of colored particles which are fast to water and other solvents; 4-aminofluorescein suitable for producing fluorescent particles; aminosilanes used to render the particles oleophilic; and p-aminobenzoic acid and its derivatives, and benzophenone compounds having phenolic hydroxyl group, which are used for the preparation of powdery ultraviolet absorbers.

As a result of chemical modification described above, the epoxide groups in the molecule will be partly or wholly lost. If all the epoxide groups are modified, the resultant molecule lacks in ability of reacting with the curing agent in the subsequent step, remaining in the form of a low molecular weight substance. Presence of such low-molecular substances in the final particles is unfavorable because of possible elution and other troubles. To minimize such disadvantages it is preferable, when all the epoxide groups in the molecule are to be modified, to use a compound having at least two epoxide groups, and to employ, as a modifier, a compound having a plurality of group capable of reacting with epoxide group or a plurality of active hydrogens, thereby increasing the molecular weight of the resulting reaction product. It is needless to say that such considerations are unnecessary when only part of the epoxide groups in the molecule is chemically modified.

When preparing the aqueous emulsion of uncured epoxy compound in the process of this invention, the modified epoxy compound as described above may be contained in an amount not larger than about 40% based on the weight of the compound having at least two epoxide groups in the molecule. If the amount exceeds this level, it is often difficult to obtain cured particles in spherical form or the formed particles will be tacky in some cases. The modified epoxy compound can be added in an amount as defined above by several ways; for example, by direct reaction of a predetermined amount of modifier with the compound having at least two epoxide groups, or by adding a necessary amount of modified epoxy compound previously prepared.

This invention also involves a method in which other inorganic or organic particles which will serve various purposes are incorporated in the particles of uncured epoxy resin emulsion, thereby producing cured epoxy compound spherical particles containing such particles. This method will be detailed below. The inorganic or organic particles to be incorporated are uniformly dispersed in the epoxy compound before emulsification. Typical examples of inorganic particles include inorganic pigment, such as titanium dioxide, calcium carbonate, ferrite, chromium hydroxide, talc, clay, silica and zinc oxide, water-insoluble metal oxides, metal sulfides, salts insoluble in water, and carbon black. The organic particles include organic pigment of phthalocyanine and azo types, and oil-soluble dyes which are insoluble in water.

The surface of these particles should preferably be oleophilic rather than hydrophlic, because higher affinity with the epoxy compound ensures easier dispersion.

It is preferred that the size of these inorganic or organic particles is less than the average size of the fine particles of cured epoxy resin of this invention. The size should preferably be less than half of the size of intended epoxy resin particles, and more preferably less than 0.5 μm.

Although there is no limitation on the amount of these inorganic or organic particles, it is preferable to use in an amount not larger than 300% based on the weight of epoxy compound. If the amount exceeds this level, much of the added particles will get out of the emulsion particles in the emulsification and curing steps.

The fine particles of cured epoxy resin of this invention may contain other additives in an amount not to defeat the intended purpose of the invention.

One example is ultraviolet absorbers, of which p-aminobenzoic acid, n-butyl-p-aminobenzoate, 2,4-dihydroxybenzophenone and 2-(2-hydroxy-5-methylphenyl)-2H-benzotriazole are preferably used.

p-Aminobenzoic acid, which is solid at normal temperature, is preferably applied to the epoxy compound in the form of solution in ethanol or acetone, followed by removal of the solvent by vacuum evaporation or other method. n-Butyl-p-aminobenzoate, 2,4-dihydroxybenzophenone and 2-(2-hydroxy-5-methylphenyl)-2H-benzotriazole, which melt at relatively low temperatures, can be dissolved in the epoxide compound by intimate mixing and subsequent heating. The preferable amount of these ultraviolet absorbers is less than 40% based on the weight of the compound having at least two epoxide groups in the molecule.

Other additives that may be used include antistatic agents, electroconductive agents and blowing agents, which are normally added to the epoxy compound before or during emulsification.

In the process of this invention the uncured epoxy resin must be emulsified in water in the presence of a surface-active agent.

Any types of surface-active agents may be used for this purpose, but use of an emulsifier having an HLB value not lower than 12 is preferable.

Typical examples include ether-type nonionic surface-active agents, such as polyoxyethylene phenol ethers and polyoxyethylene-polyoxypropylene block polyethers, ester-type nonionic surface-active agents, such as polyethylene glycol higher fatty acid esters, and fatty acid esters of polyhydric alcohols, and alkoxylated rosins. Polyamideamines which are of the self-emulsifiable type and can serve as a curing agent for epoxy compounds, such as reaction products between dimer acids and polyetherdiamines or aliphatic polyamines, may also be used advantageously.

These surface-active agents are preferably added in an amount more than 5%, more preferably more than 10%, based on the weight of epoxy compound. If the amount of emulsifier added is smaller, the stability of the uncured epoxy resin emulsion will be lower, failing to give satisfactory cured resin particles in some cases. There is no upper limit for the amount of surface-active agent used, but it is generally preferable that the amount does not exceed 30% based on the weight of epoxy compound to obtain cured resin particles with satisfactory mechanical properties.

The ease with which a liquid is emulsified is generally dependent upon its viscosity; it is difficult to emulsify a highly viscous epoxy compound or a solid type epoxy compound by mechanical force alone. In such cases, use of a solvent for epoxy compound together with a surface-active agent is advisable.

Typical solvents which may be used for this purpose include ketones, alcohols, Cellosolve solvents, 1,4-dioxane, aromatic hydrocarbons, and esters such as ethyl acetate.

In the process of this invention, the epoxy compound is emulsified in usual ways by the aid of a surface-active agent as mentioned above in the presence of a solvent as required. A typical method of emulsification will be described below.

An epoxy compound containing a surface-active agent is agitated at a high speed while being maintained at a temperature in the range from normal temperature to 95° C., and water heated to the same temperature as above is slowly added. It is generally preferable to add the water intermittently, rather than continuously. A w/o type emulsion is first formed by this method, which is then converted to an o/w type emulsion through phase conversion. High-speed agitation is recommended during and after phase conversion to obtain a stable and uniform emulsion with small particle size.

The particle size and stability of epoxy resin emulsion is closely correlated to emulsion concentration. Too low a concentration tends to poor stability, resulting in coagulation. A general notion is that concentration should be in the range of 10 to 80% by weight to obtain a satisfactory emulsion. However, the process of this invention specifies no such limitation.

The epoxy compound emulsion prepared by the method described above is stabilized by the action of the surface-active agent added, but it is effective in further enhancing emulsion stability to add, in advance, in the water used for emulsification a substance which behaves as a protective colloid, such as hydroxyethylcellulose, carboxymethylcellulose, gum arabic and polyvinyl alcohol.

Any water-soluble amines may be used as the curing agent in the process of this invention. However, it is preferable to employ such an amine as to give a cured product having a Shore A hardness not lower than 70 when it is mixed with the epoxy compound being used in equivalent quantities and the mixture is allowed to stand at normal temperature (about 20° C.) for eight hours. Such water-soluble amines include, among others, piperazine derivatives, hydrazine derivatives, polyalkylenepolyamines such as ethylenediamine, diethylenetriamine and triethylenetetramine, alcohol-amines such as ethanolamine, N-(2-aminoethyl)piperazine, and m-xylylenediamine. Particularly preferred amines are the piperazine derivatives represented by the following general formula (I) and hydrazine derivatives represented by the following general formula (II):

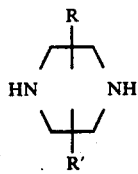
(I)

(wherein R and R' are each hydrogen or an alkyl group of 1 to 4 carbon atoms),

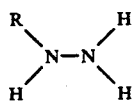
(II)

(wherein R is hydrogen, an alkyl of 1 to 5 carbon atoms, phenyl, or 2-hydroxyethyl group).

The suitable amount of the water-soluble amine may vary depending on its type, but more than 0.15 equivalent, relative to the epoxide group, is generally preferable. For piperazine, it is preferably more than 0.15 equivalent, more preferably 0.2 equivalent or more; for hydrazine, it is preferably 0.2 equivalent or larger, more preferably 0.25 equivalent or larger; and for other water-soluble amines, it is preferably 0.5 equivalent or larger, more preferably 0.6 equivalent or larger.

The upper limit for the amount of curing agent is not specified in this invention. However, an amount not larger than 4 equivalent is generally preferable because emulsion stability tends to lower with increasing amount of curing agent.

Generally, the amine curing agent is directly added to the emulsion of uncured epoxy compound in the process of this invention. But it may also be added in the form of solution in water, alcohol or other water-soluble solvent.

The concentration of emulsion to be submitted to the curing step is not specified in this invention, but is preferably higher than 5% by weight to ensure its stability. Too high a concentration, however, tends to cause coagulation during curing due to increased chances of collision among particles. Hence it is preferable that the emulsion concentration does not exceed 80% by weight.

The reaction between an epoxy compound and its curing agent is generally exothermic, which is favorable in that the heat evolved helps increase the reaction rate. However, since elevated temperature tends to adversely affect the stability of emulsion under curing, it is preferable that the temperature is held below 70° C. by external cooling for some time after addition of the curing agent. It is also advisable in some cases to add the curing agent in small portions continuously or intermittently. The temperature may be raised to 70° C. or higher in the later stage of reaction to ensure complete cure.

While curing is in progress, the emulsion should preferably be allowed to stand undisturbed or held with mild stirring to obtain satisfactory cured particles. Although depending on the extent of cure, the cured particles thus obtained may sometimes be unsatisfactory in resistance to heat and solvents. This is probably due to the fact that, in the process of this invention, curing progresses heterogeneously from the surface of each particle, which makes it difficult to put curing reaction to completion in some cases. When an amine having two active hydrogen atoms is combined with a bifunctional epoxy compound, a cured product of linear structure is likely to be formed, which may not be absolutely satisfactory for some end uses in which high resistance to heat or solvents is required.

The cured epoxy resin spherical particles of this invention may be after-treated as described below to meet special requirements for certain of their end uses. The cured particles can be heated at temperatures of 40° C. or higher, more preferably at temperatures of 50° C. or higher, to improve their resistance to heat and solvents. Although there is no upper limit for the heating temperature, it is generally preferable to heat them at temperatures below 200° C. Any known heating methods may be used for this purpose. Listed below are typical processes, in which cured particles mean the particles which have been cured to such an extent that sticking of one particle to another does not occur at normal temperature.

(1) Heating the emulsion containing both cured particles and unreacted curing agent.

(2) Separating cured particles from the emulsion, redispersing them in water or an inert solvent, and heating the resulting dispersion.

(3) Separating cured particles from the emulsion, and heating them in the subsequent drying step or after drying.

When the redispersed particles are heat-treated, redispersion should be complete to prevent particle coalescence. When the heat treatment is performed at temperatures higher than 50° C., it is often preferable to raise the temperature in steps in order to avoid particle coalescence. There is no limitation on the heat treatment time; normally, heating should be continued until intended resistance to heat and solvents is achieved. The treating time can generally be reduced by adopting higher treating temperature.

The curing reaction in the process of this invention presumably proceeds from the surface of each particle in the emulsion. Since the molecules of curing agent dissolved in the liquid phase gradually permeate inside each particle through its surface, long time is required until all the molecules of epoxy compounds are completely cured. The rate of permeation and reaction of curing agent can be increased by raising the temperature of the system in the middle or final stage of reaction, but nevertheless unreacted epoxide groups are likely to remain at the center of each particle.

These epoxide groups left unreacted even in the final stage of curing can be destroyed by treating the spherical particles with an aqueous solution of acidic substance before or after drying. Typical examples of the acidic substances used for this purpose include inorganic acids such as sulfuric, hydrochloric, nitric, phosphoric and perchloric acids, acidic salts such as aluminum sulfate and chloride, and carboxylic acids such as formic and acetic acids.

The required amount of these acidic substances may be very small because they serve as a catalyst for the reaction of water with epoxide groups, but the reaction can be put to completion in shorter time when a larger amount is added. The aqueous solution used for this acid treatment may also contain a water-miscible solvent, such as 1,4-dioxane, ethanol, methanol, Methyl Cellosolve, acetone, methyl ethyl ketone and tetrahydrofuran. The amount of water does not matter so long as it is larger than the stoichiometric quantity.

The above-mentioned treatment is preferably carried out by mixing the slurry of particles, or dried particles, with an acidic solution and thoroughly agitating the mixture.

The suitable amount of the acidic substance to be used in this treatment may vary depending on the amount of residual epoxide groups and the end use of spherical epoxy resin particles, but is normally in the range of 0.001 to 1 mole per gram of the particles.

The fine particles of cured epoxy resin of this invention can be used as an ingredient of cosmetic and other compositions; and coloring their surfaces is often demanded in such applications.

The particles of this invention are readily dyeable. Methods of dyeing are described below. The particles to be dyed may be those which have been subjected to heat treatment for improving thermal resistance or to acid treatment for destroying residual epoxide groups, or those not subjected to such treatments.

When the particles are dry, they are dispersed in a liquid capable of dissolving or finely dispersing the dye to be applied, such as water and alcohols. Use of a small amount of surface-active agent is effective in ensuring satisfactory dispersion in many cases. Intended dispersion can be achieved in shorter time if a dispersing device, such as a homogenizer, is used. Dyeing of the particles can be effected by nearly the same method as dyeing of textiles under nearly the same conditions. Any dyes reacting with amino or hydroxyl groups as active sites may be used for this purpose, including oil-soluble dyes. Of these, acid dyes and reactive dyes are particularly preferable, which give colored products difficult to decolorize by water and organic solvents. Unlike textile dyeing, collection of colored products from the dye liquor is not so easy, but this can be effected by filtration or centrifugal separation.

All the particles must be discrete from one another during dyeing operation. If coalescence occurs in a certain degree, the internal part of the aggregates will be difficult to dye. In general, wet particles which have not been dried are easier to disperse, and high degree of redispersion can be achieved by simple methods.

When an acid dye is used, the pH of dye liquor must be kept below 7. A slightly larger amount of an acid such as sulfuric or acetic acid should be used in the case of the particles of this invention because of the amino groups contained. Use of an acid dye, though depending on dyeing conditions, has an additional advantage that the unreacted epoxide groups left inside the particles may be destroyed by the catalytic action of hydrogen ion.

Dyed particles are separated from dye liquor by filtration or other suitable method, and washed. When an acid dye is used, the dyed particles contain sulfuric, acetic or other acid, which should be neutralized by adding ammonia or other alkali to the dye liquor before filtration or to the redispersing liquor after filtration. The ammonia or other alkali must be added slowly not to cause unusual rise of pH at any moment. A pH value higher than 7 can release the fixed acid dye from the particles.

Means of improving color fastness commonly used in textile dyeing, such as tannic acid treatment in acid dyeing, can be applied to the dyeing of the particles of this invention.

The colored epoxy resin particles thus obtained have high color fastness; when used as an ingredient of cosmetics, for example, there is no danger of the released dye staining the skin.

The spherical particles of epoxy resin, which have been cured and subjected to heat treatment, acid treatment or dyeing, can be recovered in the form of powder after separation from water by filtration or centrifugation. Slight particle coalescence may occur during curing in some cases. If this happens, treatment of the slurry with a homogenizer or mixer equipped with high-speed rotary blades will readily restore good dispersion. The cake of fine particles thus obtained is dried in air or by heating, giving dry particles. When the particle size is very small or the wet cake has a high moisture content, coagulation is likely to occur, some times requiring slight milling after drying.

Fine particles of cured epoxy resin can be produced by the process of this invention in a spherical or nearly spherical form having an average particle size not larger than 50 μm. The lower limit of size, though not specified, is normally 0.1 μm or larger.

The inorganic or organic particles, when formulated, are contained in the surface or inner layer of each particle. Most commonly, most of these particles are present in the surface layer. In such cases, slight unevenness is often observed on the surface, but these particles are fixed to the cured epoxy resin inside.

The cured epoxy resin particles of this invention can be used as a component of pressure-sensitive, conductive rubber and conductive adhesives, and the surface of each particle must be given electroconductivity for such applications.

The surface of the particles of this invention can be subjected to electroless plating. This treatment is normally carried out using a slurry of dry resin particles redispersed in water or a slurry of wet resin particles redispersed in water after filtration and washing. The latter type of slurry, in which all the particles remain discrete from one another, is more preferable, which is likely to give spherical particles after plating, with less tendency of plating as aggregate form.

Methods of electroless plating commonly used for plastics may be advantageously employed, with no need for the degreasing and etching steps.

The plated particles thus obtained are lighter in weight than conventional products incorporating metal powder, and can be used for applications in which the same degree of electroconductivity as conventional products is required.

As may be apparent from the foregoing, fine spherical particles of cured epoxy resin having an average size not larger than 50 μm can be easily produced by the process of this invention. The spherical particles thus produced can be used as such, or after being subjected to heat treatment, acid treatment, dyeing and plating, for the following applications: as ingredient of coatings and cosmetics, toners (particularly color toners) for electrostatic copiers, spacer for liquid-crystal, component of adhesives and pressure-sensitive conductive rubber, and medical reagents.

EXAMPLE 1

Ten grams of commercial bisphenol-A diglycidyl ether type epoxy resin (Epikote 828; Yuka-Shell Epoxy Kabushiki Kaisha; epoxy equivalent: approximately 190) was placed in a 100-ml polyethylene cup, commercial polyoxyethylene phenol ether type surface-active agent (Noigen EA-137; Dai-ichi Kogyo Seiyaku Co., Ltd.; HLB: 13) was added in varying amounts, and the mixture was kneaded for four minutes with a stirring rod fitted with Teflon blade at its tip at a rotating speed of 800 rpm. Six milliliters of water put in a syringe was then added in 1.5-ml portions at one-minute intervals, giving a milky white emulsion of the epoxy resin.

A given amount of piperazine diluted with 8 ml of water was added to this emulsion and the mixture was homogenized under mild stirring.

This epoxy resin emulsion containing the curing agent was allowed to stand undisturbed at 25° C. for five days so that curing will proceed slowly to form spherical particles of cured epoxy resin.

The relationship between the state of curing and the amount of piperazine used is shown in the following table.

TABLE 1

| Ex. | Noigen EA-137 (% per epoxy compound) | Curing Agent Type | Equivalent | Av. Particle size (μm) | Observation after Cure |
|---|---|---|---|---|---|
| 1-1 | 8 | Piperazine | 0.17 | 12 | Good |
| 1-2 | 8 | Piperazine | 0.5 | 13 | Good |
| 1-3 | 12 | Piperazine | 0.2 | 7.0 | Good |

The average particle size was measured by using centrifugal-sedimentation-type particle size distribution analyzer, Model KAPA-500 (Horiba Seisakusho).

EXAMPLE 2

One hundred grams of commercial bisphenol-A type epoxy resin (Epikote 828; Yuka-Shell Epoxy Kabushiki Kaisha; epoxy value: 190) was mixed well with 5 g of commercial nonionic surface-active agent (NS-230; Nippon Oil & Fats Co., Ltd.; HLB: 17.1), 25 g of water was added to this mixture in 5 g portions with vigorous stirring, giving an epoxy resin emulsion of about 77% concentration. To 20 g of this emulsion was added an aqueous solution of curing agent consisting of piperazine and N-(2-aminoethyl) piperazine in a given proportion, and the mixture was kept at 40° C. for two days with mild stirring to complete curing.

As may be seen from Table 2, fine spherical particles of cured epoxy resin with an average size of about 4 μm was obtained in each case.

TABLE 2

| Ex. | Concentration during Cure (%) | Eq. Amt. of Curing Agent | | Observation after Cure |
|---|---|---|---|---|
| | | Piperazine | N—(2-aminoethyl)-piperazine | |
| 2-1 | 62 | 1.0 | 0 | Uniform particles with av. size of 4 μm |
| 2-2 | 62 | 0.8 | 0.2 | Uniform particles with av. size of 4 μm |
| 2-3 | 62 | 0.5 | 0.5 | Uniform particles with av. size of 4 μm |
| 2-4 | 62 | 0.2 | 0.7 | Uniform particles with av. size of 4 μm |

EXAMPLE 3

Ten grams of commercial bisphenol-A diglycidyl ether type epoxy resin (Epikote 828) was placed in a 100-ml polyethylene cup, 0.8 g of commercial polyoxyethylene phenol ether type surface-active agent (Noigen EA-137; Dai-ichi Kogyo Seiyaku Co., Ltd.; HLB: 13) was added, and the mixture was kneaded for one minute with a stirring rod fitted with Teflon blade at its tip at a rotating speed of 800 rpm. Six milliliters of water put in a syringe was then added in 1.5-ml portions at one-minute intervals under the same stirring condition, giving 16.8 g of a milky white emulsion of the epoxy resin.

A given amount of hydrazine hydrate ($H_2NNH_2 \cdot H_2O$; amine equivalent: 12.5) diluted with 8 ml of water was slowly added to this emulsion under mild stirring, and the mixture was allowed to stand undisturbed at 25° C. for ten days to complete cure. State of curing were observed with varying amounts of hydrazine hydrate. The result is summarized in Table 3. Observation under an electron microscope revealed that spherical particles with an average size of 5 to 8 μm were formed in all cases.

TABLE 3

| | Hydrazine Hydrate Added | | Observation after Cure | |
|---|---|---|---|---|
| Ex. | Weight (g) | Equivalent | After 4 Days | After 10 Days |
| 3-1 | 1.32 | 2 | Good | Good |
| 3-2 | 0.66 | 1 | Good | Good |
| 3-3 | 0.16 | 0.25 | Good | Good |

EXAMPLE 4

Ten grams of commercial bisphenol-A diglycidyl ether type epoxy resin (Epikote 828) was placed in a 100-ml polyethylene cup, commercial polyoxyethylene phenol ether type surface-active agent (Noigen EA-137; HLB: 13) was added in varying amounts, and the mixture was kneaded for one minute with a stirring rod fitted with Teflon blade at its tip at a rotating speed of 800 rpm. Six milliliters of water put in a syringe was then added in 1.5-ml portions at one-minute intervals under the same stirring condition, giving a milky white emulsion of the epoxy resin.

A given amount of N-(2-aminoethyl)piperazine diluted with 8 ml of water was slowly added to this emulsion, and the mixture was homogenized under mild stirring.

An equivalent mixture of Epikote 828 and N-(2-aminoethyl)piperazine shows a Shore A hardness of 80 after eight hours of standing at room temperature.

The epoxy resin emulsion containing N-(2-aminoethyl)piperazine obtained above was allowed to stand undisturbed at 25° C. for ten days to form spherical particles of cured epoxy resin.

The relationship between the observation of emulsion after cure and the amounts of surface-active agent and curing agent added is shown in Table 4, in which the values for the average particle size are those measured on the slurry before drying using centrifugal-sedimentation-type particle size analyzer, Model CAPA-500 (Horiba Seisakusho).

TABLE 4

| | Noigen EA-137 (% per Epikote 828) | N—(2-aminoethyl)-piperazine (equiv.) | Observation after Cure | |
|---|---|---|---|---|
| Ex. | | | Av. Particle size (μm) | Observation |
| 4-1 | 12 | 0.6 | 2.8 | Good |
| 4-2 | 20 | 0.8 | 1.4 | Good |

EXAMPLE 5

Ten grams of Epikote 828 was placed in a 100-ml polyethylene cup, commercial polyoxyethylene alkylphenyl ether type surface-active agent (Emulsit 49; HLB: 20.5) was added in varying amounts, and emulsification was carried out in the same manner as Example 4.

A given amount of diethylenetriamine diluted with 15 ml of water was slowly added to this emulsion, and the mixture was homogenized under mild stirring.

An equivalent mixture of Epikote 828 and diethylenetriamine shows a Shore A hardness of 85 after eight hours of standing at room temperature.

The epoxy resin emulsion containing diethylenetriamine obtained above was allowed to stand undisturbed at 25° C. for six days to form spherical particles of cured epoxy resin.

The relationship between the observation of emulsion after cure and the amounts of surface-active agent and curing agent added is shown in Table 5.

TABLE 5

| | Emulsit 49* (% per Epikote 828) | Diethylenetriamine (Equiv.) | Observation after Cure | |
|---|---|---|---|---|
| Ex. | | | Av. Particle Size (μm) | Observation |
| 5-1 | 12 | 0.6 | 3.5 | Good |
| 5-2 | 16 | 1.0 | 2.1 | Good |

*On effective component basis

EXAMPLE 6

Ten grams of Epikote 828 was placed in a 100-ml polyethylene cup, a given amount of p-aminobenzoic acid was added, and the reaction between the epoxy resin and p-aminobenzoic acid was carried out at 100° C. for four hours on a hotplate equipped with a magnetic stirrer. After cooling, Noigen EA-137 (HLB: 13) was added in varying amounts, and the mixture was kneaded for one minute with a stirring rod fitted with Teflon blade at its tip at a rotating speed of 800 rpm. Six milliliters of water put in a syringe was then added in 1.5-ml portions at one-minute intervals under the same stirring condition, giving a milky white emulsion.

Given amounts of piperazine and hydrazine hydrate diluted with 8 ml of water were added to this emulsion, and the mixture was homogenized under mild stirring.

The epoxy resin emulsion containing the curing agent thus obtained was allowed to stand undisturbed at 25° C. for ten days so that curing will proceed slowly to form spherical particles of cured epoxy resin.

The relationship between the observation of emulsion after cure versus the amounts of p-aminobenzoic acid, piperazine and hydrazine hydrate added is shown in Table 6. The slurry obtained in Example 6—6 was filtered and the powder of cured epoxy resin was collected by washing and drying. Observation of this powder under an electron microscope revealed that each particle consists of finer particles aggregated into a spherical form with grained surface.

Separately, the slurry obtained in Example 6—6 was filtered through No. 5C filter paper (Toyo Roshi Co., Ltd.), the collected cake was washed and redispersed in 300 ml of water, 10 g of $4N-H_2SO_4$ was added to the dispersion, and the mixture was heated at 95° C. for four hours with mild stirring to destroy the epoxide groups left unreacted in the cured particles. The treated dispersion was collected by filtration through No. 5C filter paper, washed and redispersed in 300 ml of water, and $1N-NH_4OH$ was added until the pH rises to 9. The resulting slurry was again filtered through No. 5C filter paper, and the cake was washed and dried at 40° C. in a hot-air dryer. UV analysis (KBr disk) of the powder thus obtained showed that the maximum absorption peak has been shifted to 320 nm from 290 nm observed with p-aminobenzoic acid. This indicates that p-aminobenzoic acid is chemically fixed inside each particle through reaction with the epoxide group.

TABLE 6

| Ex. | p-Amino-benzoic acid (g) | Noigen EA-137 (% per epoxy) | Curing Agent Type | Equiv. | Av. Particle size (μm) | Observation after Cure |
|---|---|---|---|---|---|---|
| 6-1 | 0.5 | 5 | Piperazine | 0.2 | 5.2 | Good |
| 6-2 | 0.5 | 10 | Piperazine | 0.2 | 2.8 | Good |
| 6-3 | 0.5 | 5 | Hydrazine | 0.25 | 5.2 | Good |
| 6-4 | 0.5 | 10 | Hydrazine | 0.25 | 2.5 | Good |
| 6-5 | 1.0 | 5 | Piperazine | 0.17 | 4.6 | Good |
| 6-6 | 1.0 | 5 | Piperazine | 1.0 | 5.0 | Good |
| 6-7 | 1.0 | 5 | Hydrazine | 0.22 | 4.5 | Good |
| 6-8 | 1.0 | 5 | Hydrazine | 1.0 | 4.9 | Good |

EXAMPLE 7

Fifteen grams of commercial 2,4-dihydroxybenzophenone UV absorber (ASL23; Shonan Chemical Co., Ltd.) was added to 300 g of Epikote 828, and the mixture was heated at 120° C. for six hours to effect chemical modification of Epikote 828.

Thirty grams of Noigen EA-137 was added to this reaction product, the mixture was transferred to a 1-liter container of homogenizer (Nihon Seiki Kaisha Ltd.) and stirred for five minutes at a speed of 2,000 rpm while being externally heated at 50° C. Water (180 ml) was then added in 45-ml portions at 4-minute intervals by using a tubing inserted through the small hole in the cover of the container to effect emulsification.

A given amount of piperazine dissolved in 250 g of water was added to the emulsion prepared above, the mixture was homogenized under mild stirring and transferred to a 1-liter polyethylene beaker, in which it was allowed to stand undisturbed at 25° C. for five days.

The relationship between the observation of emulsion after cure and the amount of piperazine added is shown in Table 7. Spherical particles of cured epoxy resin incorporating 2,4-dihydroxybenzophenone chemically fixed therein were obtained in each case.

TABLE 7

| Ex. | Piperazine (Equivalent) | Av. Particle (μm) | Observation |
|---|---|---|---|
| 7-1 | 0.17 | 6.5 | Good |
| 7-2 | 1.0 | 6.1 | Good |

EXAMPLE 8

Ten grams of Epikote 828 was placed in a 100-ml polyethylene cup, 6 g of commercial titanium dioxide (Tipaque CR-60; Ishihara Sangyo Kaisha, Ltd.; average particle size: 0.2 μm) and a varying amount of Noigen EA-137 (HLB: 13) were added, and the mixture was kneaded for four minutes with a stirring rod fitted with Teflon blade at its tip at a rotating speed of 800 rpm. Six milliliters of water put in a syringe was then added in 1.5-ml portions at one-minute intervals under the same stirring condition, giving a milky white emulsion.

Given amounts of piperazine and hydrazine hydrate diluted with 8 ml of water were added to this emulsion, and the mixture was homogenized under mild stirring.

The epoxy resin emulsion containing the curing agent thus obtained was allowed to stand undisturbed at 25° C. for five days so that curing will proceed slowly to form spherical particles of cured epoxy resin.

The relationship between the observation of emulsion after cure versus the amounts of Noigen EA-137, piperazine and hydrazone hydrate added is shown in Table 8.

Each slurry of cured epoxy resin prepared above was transferred to a 200-ml container of homogenizer (Nihonseiki Kaisha Ltd.), 80 ml of water was added, and the diluted slurry was treated at a speed of 10,000 rpm for one minute. After removing coarse particles with a 100-mesh stainless steel screen, the slurry was filtered through No. 5C filter paper (Toyo Roshi), and the collected cake was washed and redispersed in water. $4N-H_2SO_4$ was added to the dispersion to a final acid concentration of 0.4N, and the acidified slurry was heated at 90° C. for four hours to destroy the residual epoxide groups. After neutralization with ammonia, the cured epoxy resin particles were collected by filtration through No. 5C filter paper, washed and dried. The white, fine particles thus obtained felt smooth when rubbed between fingers. Electron microscopic observation of the cross-section of a particle using an extremely thin slice showed that most of the titanium dioxide particles are present in the surface layer, with part of them being exposed on the surface of each epoxy resin spherical particle. This is in accord with the fine surface unevenness observed under a scanning-type electron microscope.

TABLE 8

| Ex. | Noigen EA-137 (% per epoxy) | Curing Agent Type | Equivalent | Av. Particle size (μm) | Observation |
|---|---|---|---|---|---|
| 8-1 | 8 | Piperazine | 0.17 | 12 | Good |
| 8-2 | 8 | Piperazine | 0.5 | 13 | Good |
| 8-3 | 12 | Piperazine | 0.1 | 6.5 | Good |
| 8-4 | 12 | Piperazine | 0.2 | 7.0 | Good |
| 8-5 | 8 | Hydrazine | 0.23 | 10 | Good |
| 8-6 | 8 | Hydrazine | 1.0 | 12 | Good |
| 8-7 | 10 | Hydrazine | 0.25 | 8.4 | Good |

EXAMPLE 9

Eight grams of Epikote 828 and two grams of Epikote 1002 were placed in a 100-ml polyethylene cup, 5 g of ferrite (BL-120; Taitan Kogyo Kabushiki Kaisha; average particle size: 0.3 μm) and a varying amount of Emulsit 100 (HLB: 22.3) were added, the mixture was heated to 80° C., and emulsification was carried out in the same manner as Example 1.

Given amounts of N-(2-aminoethyl)piperazine or monoethanolamine diluted with 8 ml of water were added to this emulsion, and the mixture was homogenized under mild stirring. The epoxy resin emulsion containing the curing agents thus obtained was allowed to stand undisturbed at 25° C. for six days so that curing will proceed slowly to form spherical particles of cured epoxy resin.

The relationship between the observation of emulsion after cure versus the amounts of surface-active agent and curing agent added is shown in Table 9. Spherical particles of cured epoxy resin incorporating ferrite fixed therein were obtained in each case.

The above-mentioned mixture of Epikote 828 and 1002, when reacted with an equivalent amount of N-(2-aminoethyl) piperazine and monoethanolamine, shows a Shore A hardness of 83 and 75, respectively, after eight hours of standing at room temperature.

TABLE 9

| Ex. | Emulsit 100 (% per epoxy) | Curing Agent Type | Equivalent | Observation after Cure Av. Particle size (μm) | Observation |
|---|---|---|---|---|---|
| 9-1 | 7 | NAEP* | 0.55 | 15 | Good |
| 9-2 | 7 | NAEP* | 1.0 | 17 | Good |
| 9-3 | 20 | NAEP* | 2.0 | 3.2 | Good |
| 9-4 | 7 | Monoethanolamine | 0.6 | 14 | Good |
| 9-5 | 7 | Monoethanolamine | 1.5 | 14 | Good |
| 9-6 | 25 | Monoethanolamine | 1.5 | 2.9 | Good |

*NAEP: N—(2-aminoethyl)piperazine

EXAMPLE 10

Ten grams of Epikote 828 was placed in a 100-ml polyethylene cup, and 1 g of n-butyl p-aminobenzoate was added at 80° C. with stirring, which readily dissolved in the epoxy resin. Noigen EA-137 (0.8 g) was added, the mixture was kneaded for one minute with a stirring rod fitted with Teflon blade at its tip at a rotating speed of 800 rpm, and 6 ml of water put in a syringe was then added in 1.5-ml portions at one-minute intervals, giving a milky white emulsion.

Eight milliliters of aqueous solution containing 0.8 equivalent amount of piperazine was added to this emulsion, and curing was carried out at 25° C. for five days, yielding a slurry containing spherical particles with an average size of 4.6 μm incorporating n-butyl p-aminobenzoate fixed therein.

EXAMPLE 11

Ten grams of Epikote 828 was placed in a 100-ml polyethylene cup, 0.8 g of Noigen EA-137 (HLB: 13) was added, the mixture was kneaded for one minute with a stirring rod fitted with Teflon blade at its tip at a rotating speed of 800 rpm, and 6 ml of water put in a syringe was then added in 1.5-ml portions at one-minute intervals under the same stirring condition, giving a milky white emulsion.

A given amount of piperazine diluted with 8 ml of water was added to this emulsion, and the mixture was homogenized under mild stirring.

The epoxy resin emulsion thus obtained was allowed to stand undisturbed at 25° C. for five days, giving a slurry of spherical particles with an average size of about 6 μm.

The cured particles thus obtained were collected by suction filtration through a filter paper, redispersed in water after washing, and the dispersion was heat-treated under the conditions shown in Table 10. The treated particles were collected by filtration, and the dried powder was tested for resistance to solvent. As may be apparent from Table 10, the resistance of cured epoxy resin particles is improved by heat treatment.

TABLE 10

| Ex. | Piperazine (Equivalent) | Heat Treatment | Resistance* to Solvent (Grade) |
|---|---|---|---|
| 11-1 | 0.6 | NO | B |
| 11-2 | 0.6 | 45° C. × 6 hr | A |
| 11-3 | 0.6 | 90° C. × 3 hr | A |
| 11-4 | 1.0 | NO | B |
| 11-5 | 1.0 | 45° C. × 6 hr | A |
| 11-6 | 1.0 | 90° C. × 3 hr | A |
| 11-7 | 2.0 | NO | B |
| 11-8 | 2.0 | 45° C. × 6 hr | A |
| 11-9 | 2.0 | 90° C. × 3 hr | A |

*Particles were immersed in ethanol, the solvent was evaporated at 50° C., and the resistance to solvent was evalutated as follows:
Grade A: Particles feel smooth when rubbed between fingers, with no particle coalescence.
Grade B: Particles feel rough when rubbed between fingers, with some of particles being coalesced due to soluble components involved.

EXAMPLE 12

Ten grams of commercial phenol-novolak type epoxy resin (Epikote 152; Yuka-Shell Epoxy Kabushiki Kaisha) was placed in a 100-ml polyethylene cup, 0.8 g of Noigen EA-137 was added, and emulsification was carried out in the same manner as Example 1. Eight milliliters of aqueous solution containing 0.8 equivalent amount of piperazine was added to the resulting emulsion, and the mixture was allowed to stand undisturbed at 25° C. for six days, giving a slurry of spherical particles of cured epoxy resin with an average size of about 6 μm. The cured particles were separated in the same way as Example 11, redispersed in an acidic solution shown in Table 11, and the dispersion was treated under the corresponding condition to destroy the residual epoxide groups. The presence or absence of epoxide group in the treated particles was judged by absorption peak in the vicinity of 910 cm$^{-1}$ on IR spectrum.

TABLE 11

| Ex. | Treating Solution Acid (mol) | Water (g) | Org. Solvent (g) | Treating Condition Temperature (°C.) | Time (hr) | Residual Epoxide Grp. |
|---|---|---|---|---|---|---|
| 12-1 | H$_2$SO$_4$ (0.06) | 50 | None | 90 | 2 | None |
| 12-2 | H$_2$SO$_4$ (0.06) | 30 | Acetone (20) | 50 | 3 | None |
| 12-3 | CH$_3$COOH (0.15) | 50 | None | 90 | 3 | None |

EXAMPLE 13

Ten grams of Epikote 828 was placed in a 100-ml polyethylene cup, 0.8 g of Noigen EA-137 was added, and the mixture was kneaded for one minute with a stirrer fitted with Teflon blade at its tip at a rotating speed of 800 rpm. Six milliliters of water put in a syringe was then added in 1.5-ml portions at one-minute intervals to effect emulsification.

Eight milliliters of water containing 0.8 equivalent amount of piperazine was added to the resulting emulsion, and the mixture was allowed to stand undisturbed at 25° C. for five days, giving a slurry of spherical particles of cured epoxy resin with an average size of 6.4 μm.

The cured particles were collected by suction filtration, washed, redispersed in water, and dyed under the following conditions:
Bath ratio: 1:10
Dye: Food Red No. 104 (acid dye), 2%-owf
Sulfuric acid: 4N-H$_2$SO$_4$, 7 g
Temperature: 90° C.

Time: 2 hours

Sulfuric acid was added five minutes after addition of the dye. The mixture was slowly stirred during dyeing.

The dyed particles were collected by suction filtration, redispersed in water, and 1N-NH$_4$OH was slowly added for neutralization. This operation was carried out under high-speed agitation while observing a pH meter (pH electrode), taking care that the pH of the liquor will not exceed 8.0 at any moment. Addition of ammonia was stopped when the pH reaches 5.5, and the particles were collected by suction filtration, washed and air-dried.

The dyed particles thus obtained assumed a brilliant red color, and the fixed dye was not released when treated with hot water, ethanol, propylene glycol and benzene.

EXAMPLE 14

Ten grams of Epikote 828 was placed in a 100-ml polyethylene cup, 1.0 g of Emulsit 100 was added, and emulsification was carried out in the same manner as Example 1.

Eight milliliters of water containing 1.0 equivalent amount of N-(2-aminoethyl)piperazine was added to the resulting emulsion, and the mixture was allowed to stand undisturbed at 25° C. for six days, giving a slurry of spherical particles of cured epoxy resin with an average size of 4.1 μm. An equivalent mixture of Epikote 828 and N-(2-aminoethyl)piperazine shows a Shore A hardness of 80 after eight hours of standing at 20° C.

Dyeing of the powder obtained above with Food Blue No. 1 (1%-owf) in the same way as Example 13 gave particles colored in brilliant blue.

The dyed particles were then subjected to tannic acid treatment under the following conditions:

(Bath 1)
Tannic acid: 2%-owf
Acetic acid: 0.6%-owf
Bath ratio: 1:40
Temperature: 80° C.
Time: 1 hour
(Bath 2)
Tartar emetic: 1%-owf
Acetic acid: 0.9%-owf
Bath ratio: 1:40
Temperature: 80° C.
Time: 1 hour The treated particles were immersed in a 1% aqueous solution of sodium dodecylbenzenesulfonate. Little, if any, of the fixed dye was released. In contrast, some dye releasing was observed with untreated colored particles. There was no dye releasing at all when immersed in hot water and ethanol, for both of the treated and untreated particles.

EXAMPLE 15

A slurry of cured epoxy resin particles prepared in the same way as Example 13 was filtered and washed, the collected cake was redispersed in a small amount of water, and the dispersion was subjected to silver plating according to the steps given below.

(1) Sensitizing
SnCl$_2$.2H$_2$O 30 g/l, HCl 15 ml/l;
25° C., 3 minutes (under stirring)
(2) Filtration and Washing
(3) Catalyzing
PdCl$_2$.2H$_2$O 1 g, Na$_2$SnO$_3$.3H$_2$O 1.5 g, SnCl$_2$.2H$_2$O 37.5 g, HCl 300 ml, H$_2$O 600 ml; 25° C., 3 minutes (under stirring)
(4) Filtration and Washing
(5) Accelerating HCl 100 g/l, or H$_2$SO$_4$ 70 g/l; 30° C., 4 minutes (under stirring)
(6) Filtration and Washing
(7) Electroless Copper Plating
Copper sulfate 30 g/l, Sodium carbonate 30 g/l, Potassium sodium tartarate 100 g/l, sodium hydroxide 50 g/l, 37% Formalin 30 ml/l 24° C.
(8) Filtration and Washing
(9) Silver Plating
Silver solution: Ammonia (s.g.: 0.99) was added to silver nitrate (3.5 g) until the precipitate once formed dissolves completely, and the solution was diluted with water to a total volume of 100 ml. Reducing solution: A mixture of 38%-formalin (1.1 ml), 99%-ethanol (95 ml) and water (3.9 ml). A mixture of equal volumes of the silver solution and reducing solution prepared above was used as the silver plating solution;
(10) Filtration and Washing
(11) Drying The plated particles were treated with hot nitric acid to dissolve the attached metals, and the solution was analyzed by atomic absorption spectroscopy for the contents of copper and silver. The analytical data showed 24 wt-% of copper and 25 wt-% of silver plated on the spherical particles. Observation under an electron microscope revealed that the surface of each particle is uniformly covered with the plated metal. In addition, observation of the cross-section of plated particle by means of scanning-type electron microscope/X-ray microanalyzer demonstrated that the plated metal is of the double-layer structure, with silver present in the outer and copper in the inner layer.

We claim:

1. A process for producing cured epoxy resin spherical particles having an average particle size not larger than 50 μm, which comprises mixing an uncured epoxy compound, a surface-active agent and water to prepare an emulsion of said uncured epoxy compound, said uncured epoxy compound comprising 50 to 100% by weight of a compound having at least two epoxide groups; adding a water-soluble amine to said emulsion; and curing said uncured epoxy compound.

2. The process for producing cured epoxy resin spherical particles as defined in claim 1, wherein said uncured epoxy compound has been chemically modified with an ultraviolet absorber.

3. The process for producing cured epoxy resin spherical particles as defined in claim 1, wherein said surface-active agent has an HLB value not lower than 12.

4. The process for producing cured epoxy resin spherical particles as defined in claim 1, wherein the amount of said surface-active agent is in the range of 5 to 30% based on the weight of said uncured epoxy compound.

5. The process for producing cured epoxy resin spherical particles as defined in claim 1, wherein said water-soluble amine is such an amine as to give a cured product having a Shore A hardness not lower than 70 when it is mixed with said uncured epoxy compound in equivalent quantities and the mixture is allowed to stand at normal temperature for 8 hours.

6. The process for producing cured epoxy resin spherical particles as defined in claim 1, wherein the amount of said water-soluble amine is at least 0.15 equivalent based on the epoxide groups present.

7. The process for producing cured epoxy resin spherical particles as defined in claim 1, wherein said water-soluble amine is a piperazine derivative represented by the following general formula

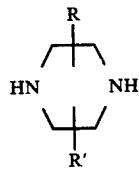

wherein R and R' are each hydrogen or an alkyl group of 1 to 4 carbon atoms.

8. The process for producing cured epoxy resin spherical particles as defined in claim 1, wherein said water-soluble amine is a hydrazine derivative represented by the following general formula

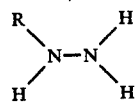

wherein R is hydrogen, an alkyl of 1 to 5 carbon atoms, phenyl, or 2-hydroxyethyl group.

9. The process for producing cured epoxy resin spherical particles as defined in claim 1, wherein the particles in said emulsion of uncured epoxy compound contain an ultraviolet absorber admixed therein.

10. The process for producing cured epoxy resin spherical particles as defined in claim 1, wherein the particles in said emulsion of uncured epoxy compound contain inorganic or organic particles having an average size smaller than that of the particles in said emulsion of uncured epoxy compound.

11. The process for producing cured epoxy resin spherical particles as defined in claim 11, wherein the average size of said inorganic or organic particles is not larger than 0.5 μm.

12. The process for producing cured epoxy resin spherical particles as defined in claim 1, wherein said spherical particles are further heat-treated at a temperature above 40° C.

13. The process for producing cured epoxy resin spherical particles as defined in claim 1, wherein said spherical particles are further treated with an acidic aqueous solution.

14. The process for producing cured epoxy resin spherical particles as defined in claim 1, wherein said spherical particles are further dyed with an acid dye or reactive dye.

15. The process for producing cured epoxy resin spherical particles as defined in claim 1, wherein said spherical particles are further subjected to electroless plating.

* * * * *